(12) United States Patent
Tanaka et al.

(10) Patent No.: US 6,906,215 B1
(45) Date of Patent: Jun. 14, 2005

(54) POWDERY S,S-ETHYLENEDIAMINE-N,N'-DISUCCINIC ACID IRON COMPLEX AND PROCESS FOR PRODUCING THE SAME

(75) Inventors: Shigeho Tanaka, Yokohama (JP); Hiroyasu Banba, Yokohama (JP); Kiyonobu Niwa, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/959,565

(22) PCT Filed: Apr. 28, 2000

(86) PCT No.: PCT/JP00/02815

§ 371 (c)(1),
(2), (4) Date: Mar. 18, 2002

(87) PCT Pub. No.: WO00/66540

PCT Pub. Date: Sep. 11, 2000

(30) Foreign Application Priority Data

Apr. 30, 1999 (JP) .......................................... 11/124595

(51) Int. Cl.$^7$ ........................... C07F 15/02; G03C 5/44; D06L 3/00
(52) U.S. Cl. ............................ 556/148; 430/461; 8/101
(58) Field of Search .............................. 556/148; 8/101; 430/461

(56) References Cited

U.S. PATENT DOCUMENTS 5,679,817 A * 10/1997 Sakai et al. .................. 556/148

FOREIGN PATENT DOCUMENTS

| EP | 0 581 197 | 2/1994 |
| EP | 0 694 528 | 1/1996 |
| JP | 7-291984 | 11/1995 |
| JP | 8-54719 | 2/1996 |
| JP | 10-1660 | 1/1998 |
| JP | 10-231469 | 9/1998 |
| WO | 99/23062 | 5/1999 |

* cited by examiner

Primary Examiner—Porfirio Nazario-Gonzalez
(74) Attorney, Agent, or Firm—Oblon, Spivak, McClelland, Maier & Neustadt, P.C.

(57) ABSTRACT

There is provided a powdery S,S-EDDS iron complex improved in its caking property. An S,S-ethylenediamine-N,N'-disuccinic acid iron complex, which is crystalline and has an average particle diameter of from 10 to 1000 μm and a water content of not more than 7% by weight, a powdery S,S-ethylene-N,N'-disuccinic acid (S,S-EDDS) iron complex having a compressive strength of not more than 1 kg/cm$^2$, the compressive strength being measured according to JIS A 1108 after a lapse of 2 months under conditions of a temperature of 50° C. and a load of 300 g/cm$^2$, and a process for producing the same.

19 Claims, 1 Drawing Sheet

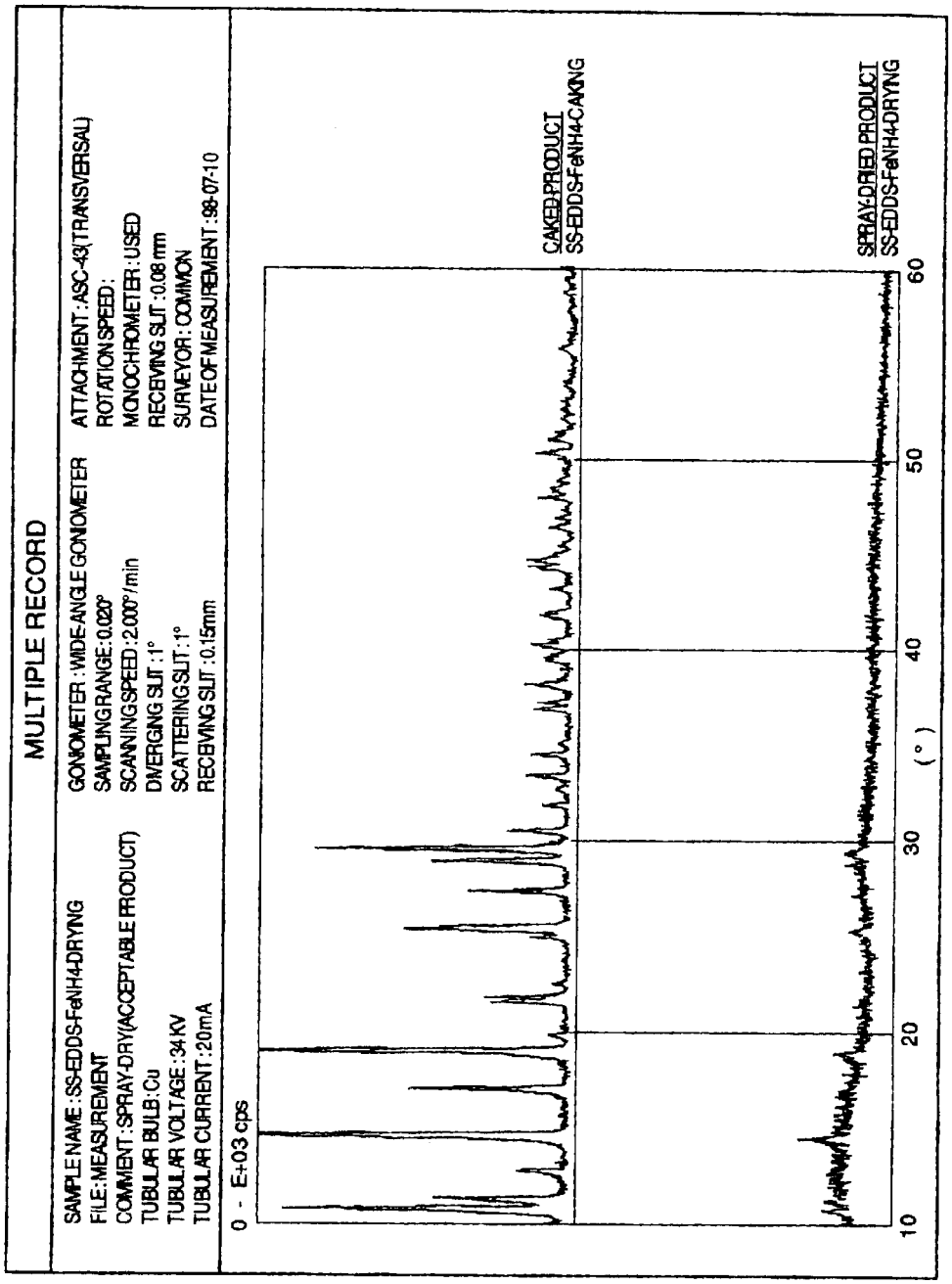

POWDERY S,S-ETHYLENEDIAMINE-N,N'-DISUCCINIC ACID IRON COMPLEX AND PROCESS FOR PRODUCING THE SAME

TECHNICAL FIELD

The present invention relates to a powdery S,S-ethylenediamine-N,N'-disuccinic acid iron complex having an improved caking property (the ethylenediamine-N,N'-disuccinic acid is hereinafter abbreviated as "EDDS"), and a process for producing the same. The S,S-EDDS iron complex is a biodegradable chelating agent useful in the field of photographic treatments, particularly in the field of photographic bleaching.

BACKGROUND ART

With respect to EDSS iron complex and a process for producing the same, for example, an EDDS ferric complex salt and a process for producing the same (JP-A-7-2745 and JP-A-7-29184) and an S,S-EDDS ferric ammonium salt and a process for producing the same (JP-A-8-34764) are known. According to these processes, a combination of EDDS (a mixture of its racemic compound and its meso compound) and an alkali metal hydroxide, or a combination of S,S-EDDS and ammonia is subjected to reaction with iron oxide or iron in an aqueous medium, and the resulting reaction product is oxidized. In addition, a production process comprising mixing an EDDS alkali metal salt and an iron salt dissolved is also known (WO 9811058).

These EDDS iron complexes can be recovered as their solid products by removing water from the aqueous reaction product solution, and then be applied mainly in the field of photographic treatments. Embodiments of applying such a solid treating agent are disclosed in, for example, JP-A-7-295162.

On the contrary, JP-A-10-1660 and JP-A-10-231469 disclose descriptions on improvements of caking properties (consolidating properties) of EDDS iron complex and S,S-EDDS iron complex, respectively.

DISCLOSURE OF INVENTION

With respect to a solid product such as powder, in general, it is often observed that a caking (consolidating) of the product occurs during a storage life of one month or more until the application thereof, even if there is no problem immediately after the production thereof. The caking problem is obliged to add unnecessary steps such as crushing and pulverization of a lump in an application thereof depending on a degree of the caking.

Based that, as the chelating agent used in the photographic treatment field, particularly in the photographic bleaching field, it is desired to develop an S,S-EDDS iron complex, which is in a solid form and superior in its biodegradability to EDDS iron complex composed of a mixture of racemic and meso compounds, the inventors of the present invention have undertaken further extensive studies on an improvement of the caking property as disclosed in the above-mentioned JP-A-10-1660 and JP-A-10-231469. As a result, it has been confirmed that the S,S-EDDS iron complex is easier to cake (consolidate) than the EDDS iron complex composed of the mixture of the racemic and meso compounds.

Accordingly, an object of the present invention is to provide a powdery S,S-EDDS iron complex improved in its caking property, so that it is difficult to cake even under severer conditions.

First of all, in order to know effects of a particle diameter and a contact area between particles of the S,S-EDDS iron complex, the present inventors have examined its caking property by dehydrating and drying the iron complex-containing aqueous solution according to a spray drying method and a fluidized bed type granulation method. As a result, it has been found that the caking is observed in the spray-dried product (having an average particle diameter of from 50 to 80 $\mu$m), but no caking is observed in the fluidized bed type granulated product (having an average particle diameter of from 300 to 600 $\mu$m).

Incidentally, the caking property was examined according to a cake strength measuring method as mentioned below.

Further, a caking property has been examined after the fluidized bed type granulated product was pulverized to obtain an average particle diameter of about 100 $\mu$m, which is close to that of the spray-dried product. In result, it has been found that no caking is observed. On the other hand, a caking property has been examined after the spray-dried product which had once caked was pulverized to obtain an average particle diameter of about 100 $\mu$m. In result, it has been surprisingly found that no caking is observed.

The present inventors have further undertaken extensive studies. As a result, it has been found that a remaining water content of the spray-dried product is from 5 to 9% by weight, whereas water contents of both the fluidized bed type granulated product and the spray-dried product which has once caked become not more than 2% by weight. In addition, as a result of examination of the powder according to an X-ray crystalline diffraction, it has been confirmed that the spray-dried product is amorphous, whereas both the fluidized bed type granulated product and the spray-dried product which has once caked become crystalline. FIG. 1 shows these results of the X-ray crystalline diffraction.

On the other hand, with respect to the powder of the EDDS iron complex composed of the mixture of the racemic compound and the meso compound, it has been found that even the spray-dried product thereof is difficult to cake as compared to the powder of the S,S-EDDS iron complex. Additionally, the fluidized bed granulated product and the spray-dried product which had somewhat caked were examined according to the X-ray crystalline diffraction, and in result, almost no crystallization was revealed.

Based on these knowledge, the present invention has been accomplished by obtaining a specific powdery S,S-EDDS iron complex and by specifying conditions under which the complex is produced.

That is, the present invention provides (1) a powdery S,S-ethylenediamine-N,N'-disuccinic acid iron complex, which is crystalline and has an average particle diameter of from 10 to 1000 $\mu$m and a water content of not more than 7% by weight, (2) the complex according to the above-mentioned item (1), wherein the water content is not more than 5% by weight, (3) a powdery [S,S]-ethylenediamine-N,N'-disuccinic acid iron complex, which has a compressive strength of not more than 1 kg/cm$^2$, the compressive strength being measured according to JIS A 1108 after a lapse of 2 months under conditions of a temperature of 50° C. and a load of 300 g/cm$^2$, (4) the complex according to the above-mentioned item (3), wherein the compressive strength is not more than 0.5 kg/cm$^2$, (5) a process for producing the powdery S,S-ethylenediamine-N,N'-disuccinic acid iron complex according to the above-mentioned item (1), (3) or (4), which comprises drying an aqueous solution containing an iron ammonium salt or iron alkali metal salt of S,S-ethylenediamine-N,N'-disuccinic acid under conditions of a drying temperature of not higher than 200° C. and a drying period of time of not less than 1 minute to obtain a dried product having a water content of not more than 7% by weight, and then pulverizing the dried product, (6) the process according to the above-mentioned item (5), wherein the drying is carried out to obtain a dried product having a water content of not more than 5% by weight, (7) the process according to the above-mentioned item (5) or (6), wherein the drying and the pulverizing are carried out with a fluidized bed type granulating machine, (8) the process according to the above-mentioned item (5) or (6), wherein the drying and the pulverizing are carried out by means of spray drying, and thereafter an additional drying is carried out, (9) the process according to the above-mentioned item (5) or (6), wherein the drying and the pulverizing are carried out by means of spray drying to obtain a powder, thereafter the powder obtained is consolidated and the product consolidated is further dried, (10) a method of using the complex according to any of the above-mentioned items (1) to (4) as a photographic treatment agent, and (11) the method according to the above-mentioned item (10), wherein the photographic treatment agent is a photographic bleaching agent.

BRIEF DESCRIPTION OF THE DRAWING

FIG. 1 shows X-ray crystalline diffraction results of a spray-dried product and a spray-dried product which has once caked, with respect to S,S-EDDS iron complex powder.

BEST MODE FOR CARRYING OUT THE INVENTION

In the present invention, the judgement of "crystalline" relies upon the results of X-ray crystalline diffraction. A "compressive strength measured according to JIS A 1108 after a lapse of 2 months under conditions of a temperature of 50° C. and a load of 300 g/cm$^2$" is defined in a cake strength measuring method as mentioned below.

The powdery S,S-EDDS iron complex in accordance with the present invention can be obtained according to a process, in which S,S-EDDS; an alkali metal hydroxide or ammonia; and iron oxide or iron are subjected to reaction with one another and then the reaction product obtained is oxidized, for example, by subjecting a ferric alkali metal salt aqueous solution or a ferric ammonium aqueous solution obtained by the process disclosed in the above-mentioned JP-A-8-34764 to dehydration, drying and pulverization. A temperature of the drying (a product temperature in the drying) is not higher than 200° C., preferably not higher than 140° C., a drying period of time is not less than 1 minute, preferably not less than 10 minutes, and a water content is not more than 7% by weight, preferably not more than 5% by weight.

A drying machine is not particularly limited. It is permitted to use any of agitation mixing type and fluidized bed type granulators or a combination of a spray dry and other drying machines. The drying may be carried out batchwise or continuously.

The "product temperature" mentioned above means an interior temperature of a drier when a box thermostat drier or an agitation mixer are used, means an interior temperature of a fluidized bed when a fluidized bed type granulation drier is used, and means an evacuation temperature when a spray drier is used. The "drying period of time" means a period of time from arrival at a predetermined temperature to taking out of a dried material when the drying is carried out batchwise, and means an average residence time in an apparatus when the drying is carried out continuously.

The "water content" means a value obtained by expressing a value in percent terms, the latter value being obtained by dividing a weight of water contained in the dried powder by a total weight of the dried powder.

The powdery S,S-EDDS iron complex obtained is crystalline and possessed of an average particle diameter of from 10 to 1000 µm and a water content of not more than 7% by weight, and further possessed of an improved caking property, which is expressed by a compressive strength of not more than 1 kg/cm$^2$, preferably not more than 0.5 kg/cm$^2$, the compressive strength being measured according to JIS A 1108 after a lapse of 2 months under conditions of a temperature of 50° C. and a load of 300 g/cm$^2$. Incidentally, the expression "no caking was observed" in Examples means that no caking was observed after storage for 1 month at a temperature of 80° C. under a pressure of 71.4 gf/cm$^2$, and the expression "caking was observed" means that caking was observed after storage for 1 month under the same conditions mentioned above.

The powdery S,S-EDDS iron complex ammonium salt in accordance with the present invention may contain at least one impurity in an amount of not more than 8% by weight, preferably not more than 6% by weight, the impurity including S,S-EDDS and unreacted materials and by-products produced in the course of production of the iron complex such as aspartic acid, maleic acid, acrylic acid, malic acid, glycine, glycolic acid, iminodiacetic acid, nitrilotriacetic acid, α-alanine, β-alanine, iminodipropionic acid, fumaric acid, ethylenediamine, ethylenediamine-N-monosuccinic acid, cyclization products of S,S-EDDS and cyclization products of ethylenediamine monosuccinic acid.

The present invention is illustrated in detail with reference to the following Examples, but the present invention is not limited to Examples, so long as the present invention is not beyond the scope thereof.

<Cake Strength Measuring Method>

It was measured according to JIS A 1108 (concrete compressive strength testing method) comprising the following (1) to (3).

(1) About 10 g of a sample is packed in a SUS made cell having an inside diameter of 25 mmφ and a separation cross-sectional area of 4.9 cm$^2$, (2) a filter paper and a perforated-plate are put on the cell, and a load of 313 g/cm$^2$ is applied thereon with a one-point press machine, and (3) the one-point press machine is put in a thermostat box of 50° C. and, after 1 month, the test piece which has caked is taken out from the cell, a load is applied to the test piece under conditions of a temperature of 25° C. and a humidity of 55% using a compressive test machine (a computer instrumentation and controls type precision all-purpose testing machine: Shimadzu Autograph AGS-100B), and a maximum load shown by the testing machine at the time of breaking the test piece is divided by a cross-sectional area of the test piece to determine a cake strength.

<Water Content Measuring Method>

A sample (A (g)) is thinly spread on a petri dish, the dish is put in a thermostat box of 120° C. and dried for 3 hours, and a weight of the sample after the drying (B (g)) is measured to determine a water content according to the following equation.

Water content (% by weight)=$(A-B)\times 100/A$

EXAMPLE 1

As a seed material, 2.50 kg of S,S-EDDS iron ammonium salt powder having a particle diameter of 50 µm, which had been dried by means of spray drying, was fed in a fluidized bed granulation drier, and the seed material was fluidized under conditions of a hot air temperature of 110° C., an interior temperature of the fluidized bed of 64° C. and an air speed of 0.85 m/s. Then, 4.8 kg of a starting material, that is, an aqueous solution containing 2.4 kg of S,S-EDDS iron ammonium salt and impurities, that is, 0.01 kg of fumaric acid, 0.01 kg of ethylenediamine, 0.10 kg of a cyclization product of S,S-ethylenediamine-N,N'-disuccinic acid, 0.02 kg of ethylenediamine-N-monosuccinic acid and 0.02 kg of ethylenediamine-N-monosuccinic acid was sprayed over 60.5 minutes. Thereafter, ventilation of hot air was further conducted for about 10 minutes and then was discontinued, and the powder was removed.

As a result, iron ammonium salt powder of the S,S-EDDS iron complex having an average particle diameter of about 500 μm and a water content of 2.06% by weight was obtained. A crystal structure of the powder was examined according to the X-ray diffraction, thereby finding a fact that the powder was crystalline. The cake strength thereof was found to be 0.1 kg/cm$^2$ and no caking was observed.

EXAMPLE 2

The same operation was carried out using the same apparatus, seed material and starting material as those in Example 1, except that drying conditions were changed.

That is, the seed material was fluidized under conditions of a hot air temperature of 150° C., an interior temperature of the fluidized bed of 110° C. and an air speed of 0.7 m/s, and then, the starting material was fed therein so as to make an average residence time about 20 minutes, thereby discharging the powder.

As a result, S,S-EDDS iron ammonium salt powder having an average particle diameter of 100 μm and a water content of 1.59% by weight was obtained. A crystal structure of the powder was examined according to the X-ray diffraction, thereby finding a fact that the powder was crystalline. The cake strength thereof was found to be 0.1 kg/cm$^2$ and no caking was observed.

EXAMPLE 3

Under conditions of a hot air inlet temperature of 180° C. and an evacuation temperature of 86° C., 28.5 kg of an S,S-EDDS iron ammonium salt 50% aqueous solution was dried over 52 minutes by means of spray drying. An average residence time in the apparatus was about 8 seconds. As a result, S,S-EDDS iron ammonium salt powder having an average particle diameter of 50 μm and a water content of 7.93% by weight was obtained. A crystal structure of the powder was examined according to the X-ray diffraction, thereby finding a fact that the powder was amorphous.

Further, the powder obtained was spread over a tray at a thickness of about 5 mm and was dried for about 3 hours in a thermostat drier of 100° C. A water content was found to be 1.8% by weight. A crystal structure of the powder was examined according to the X-ray diffraction, thereby finding a fact that the powder was crystalline. The cake strength thereof was found to be 0.2 kg/cm$^2$ and almost no caking was observed.

COMPARATIVE EXAMPLE 1

With respect to the amorphous S,S-EDDS iron ammonium salt powder having an average particle diameter of 50 μm and a water content of 7.93% by weight, which had been obtained only by the spray-drying operation described in Example 3, a cake strength thereof was measured, and as a result, the cake strength was found to be 2.0 kg/cm$^2$, and caking was observed.

COMPARATIVE EXAMPLE 2

Under conditions of a hot air inlet temperature of 180° C. and an outlet temperature of 93° C., 88.7 kg of an S,S-EDDS iron ammonium salt 50% aqueous solution was spray-dried over 313 minutes. An average residence time in the apparatus was about 16 seconds.

As a result, S,S-EDDS iron ammonium salt powder having an average particle diameter of 81 μm and a water content of 5.1% by weight was obtained. A crystal structure of the powder was examined according to the X-ray diffraction, thereby finding a fact that the powder was amorphous. The cake strength was found to be 1.5 kg/cm$^2$, and caking was observed.

COMPARATIVE EXAMPLE 3

The same operation as in Comparative Example 1 was carried out, except that the S,S-EDDS iron ammonium aqueous solution was changed to an EDDS iron ammonium salt aqueous solution composed of a mixture of its racemic compound and its meso compound (molar ratio of S,S:R, S:R,R=25:50:25).

As a result, EDDS iron ammonium salt powder having an average particle diameter of about 50 μm and a water content of 7.1% by weight was obtained. A crystal structure of the powder was examined according to the X-ray diffraction, thereby finding a fact that the powder was amorphous. The cake strength thereof was found to be 1.2 kg/cm$^2$ and caking was observed.

INDUSTRIAL APPLICABILITY

It is possible to provide a powdery SS-EDDS iron complex, which is improved in its caking property and can be easily handled without any step such as crushing and pulverization even after a long storage.

What is claimed is:

1. A powdery S,S-ethylenediamine-N,N'-disuccinic acid iron complex, which is crystalline and has an average particle diameter ranging from 10 to 1000 μm and a water content of not more than 5% by weight.

2. A powdery S,S-ethylenediamine-N,N'-disuccinic acid iron complex, which has a compressive strength of not more than 1 kg/cm$^2$, the compressive strength being measured according to JIS A 1108 after a lapse of 2 months under conditions of a temperature of 50° C. and a load of 300 g/cm$^2$.

3. The complex according to claim 2, wherein the compressive strength is not more than 0.5 kg/cm$^2$.

4. A process for producing the powdery S,S-ethylenediamine-N,N'-disuccinic acid iron complex according to claim 1, which comprises:

drying an aqueous solution containing an iron ammonium salt or iron alkali metal salt of S,S-ethylenediamine-N, N'-disuccinic acid under conditions of a product temperature of not higher than 200° C. and a drying period of time of not less than 1 minute to produce a SS-EDDS-Fe NH$_4$ salt having a water content of not more than 5% by weight and an average particle diameter ranging from 10 to 1000 μm; and then pulverizing the dried SS-EDDS-Fe NH$_4$ salt product.

5. The process according to claim 4, wherein the drying and the pulverizing are conducted with a fluidized bed type granulating machine.

6. The process according to claim 4, wherein the drying and the pulverizing are conducted by means of spray drying, said process further comprising an additional drying after drying and pulverizing.

7. The process according to claim 4, wherein the drying and the pulverizing are conducted by means of spray drying to obtain a powder, further comprising consolidating and drying said powder after drying and pulverizing.

8. A photographic treatment agent comprising the complex as claimed in claim 1.

9. The photographic treatment agent claimed in claim 12, wherein said photographic treatment agent is a photographic bleaching agent.

10. A process for producing the powdery S,S-ethylenediamine-N,N'-disuccinic acid iron complex according to claim 2, which comprises drying an aqueous solution containing an iron ammonium salt or iron alkali metal salt of S,S-ethylenediamine-N,N'-disuccinic acid under conditions of a product temperature of not higher than 200° C. and a drying period of time of not less than 1 minute to obtain a dried product having a water content of not more than 5% by weight, and then pulverizing the dried product.

11. The process according to claim 10, wherein the drying and the pulverizing are conducted with a fluidized bed type granulating machine.

12. The process according to claim 10, wherein the drying and the pulverizing are conducted by means of spray drying, said process further comprising an additional drying after drying and pulverizing.

13. The process according to claim 10, wherein the drying and the pulverizing are conducted by means of spray drying to obtain a powder, further comprising consolidating and drying said powder after drying and pulverizing.

14. A photographic treatment agent comprising the complex as claimed in claim 2.

15. The photographic treatment agent claimed in claim 14, wherein said photographic treatment agent is a photographic bleaching agent.

16. The complex according to claim 1, wherein the powdery S,S-ethylenediamine-N,N'-disuccinic acid iron complex contains at least one impurity in an amount of not more than 8% by weight.

17. The complex according to claim 16, wherein the powdery S,S-ethylenediamine-N,N'-disuccinic acid iron complex contains at least one impurity in an amount of not more than 6% by weight.

18. The complex according to claim 1, wherein the at least one impurity is selected from the group consisting of aspartic acid, maleic acid, acrylic acid, malic acid, glycine, glycolic acid, iminodiacetic acid, nitriloacetic acid, α-alanine, β-alanine, iminodipropionic acid, fumaric acid, ethylenediamine, ethylenediamine-N-monosuccinic acid, cyclization products of S,S-EDDS and cyclization products of ethylenediamine monosuccinic acid.

19. A process for producing the powdery S,S-ethylenediamine-N,N'-disuccinic acid iron complex according to claim 1, which comprises:

fluidizing an S,S-ethylenediamine-N,N'-disuccinic acid iron salt seed material in heated air; and intimately contacting the fluidized seed material with an amount of impurity containing aqueous solution of S,S-ethylenediamine-N,N'-disuccinic acid iron salt under fluidizing conditions maintained by a flow of heated air and subsequently continuing the flow of heated air at a temperature of not higher than 200° C. and a drying period of time not less than one minute to obtain a dried S,S-ethylenediamine-N,N'-disuccinic acid iron salt product having a water content of not more than 5% by weight and an average particle diameter ranging from 10 to 1000 μm.

* * * * *

UNITED STATES PATENT AND TRADEMARK OFFICE
CERTIFICATE OF CORRECTION

PATENT NO. : 6,906,215 B1
DATED : June 14, 2005
INVENTOR(S) : Tanaka et al.

It is certified that error appears in the above-identified patent and that said Letters Patent is hereby corrected as shown below:

<u>Title page,</u>
Item [87], should read:
-- PCT Pub. No.:  WO00/66540
   PCT Pub. Date:  Nov. 9, 2000 --.

Signed and Sealed this

Twentieth Day of September, 2005

JON W. DUDAS
*Director of the United States Patent and Trademark Office*